United States Patent
Seneca et al.

(10) Patent No.: US 12,138,339 B2
(45) Date of Patent: Nov. 12, 2024

(54) DYE COMPOSITION BASED ON COPOLYMERS DERIVED FROM THE POLYMERIZATION OF AT LEAST ONE CROTONIC ACID MONOMER OR CROTONIC ACID DERIVATIVE AND ON SILICONE

(71) Applicant: L'OREAL, Paris (FR)

(72) Inventors: David Seneca, Saint-Ouen (FR);
Delphine Charrier, Saint-Ouen (FR);
Sophie Bodelin, Chevilly la Rue (FR);
Melissa Lassale, Saint-Ouen (FR)

(73) Assignee: L'OREAL, Paris (FR)

( * ) Notice: Subject to any disclaimer, the term of this patent is extended or adjusted under 35 U.S.C. 154(b) by 617 days.

(21) Appl. No.: 16/623,131

(22) PCT Filed: Jun. 22, 2018

(86) PCT No.: PCT/EP2018/066801
§ 371 (c)(1),
(2) Date: Dec. 16, 2019

(87) PCT Pub. No.: WO2019/002143
PCT Pub. Date: Jan. 3, 2019

(65) Prior Publication Data
US 2020/0170919 A1 Jun. 4, 2020

(30) Foreign Application Priority Data
Jun. 30, 2017 (FR) ...................................... 1756128

(51) Int. Cl.
A61K 8/81 (2006.01)
A61K 8/06 (2006.01)
A61K 8/34 (2006.01)
A61K 8/36 (2006.01)
A61K 8/37 (2006.01)
A61K 8/891 (2006.01)
A61K 8/898 (2006.01)
A61Q 5/06 (2006.01)

(52) U.S. Cl.
CPC ............ *A61K 8/8147* (2013.01); *A61K 8/062* (2013.01); *A61K 8/342* (2013.01); *A61K 8/361* (2013.01); *A61K 8/37* (2013.01); *A61K 8/8135* (2013.01); *A61K 8/8152* (2013.01); *A61K 8/891* (2013.01); *A61K 8/898* (2013.01); *A61Q 5/065* (2013.01); *A61K 2800/21* (2013.01); *A61K 2800/43* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 2,798,053 | A | 7/1957 | Brown |
| 2,923,692 | A | 2/1960 | Ackerman et al. |
| 3,579,629 | A | 5/1971 | Pasero et al. |
| 3,810,977 | A | 5/1974 | Levine et al. |
| 3,966,403 | A | 6/1976 | Papantoniou et al. |
| 3,966,404 | A | 6/1976 | Papantoniou et al. |
| 4,185,087 | A | 1/1980 | Morlino |
| 4,237,243 | A | 12/1980 | Quack et al. |
| 4,282,203 | A | 8/1981 | Jacquet et al. |
| 4,578,266 | A | 3/1986 | Tietjen et al. |
| 4,957,732 | A | 9/1990 | Grollier et al. |
| 5,645,609 | A | 7/1997 | Andrean et al. |
| 5,955,003 | A | 9/1999 | Terren et al. |
| 5,990,479 | A | 11/1999 | Weiss et al. |
| 6,106,577 | A | 8/2000 | Audousset et al. |
| 6,159,486 | A | 12/2000 | Terren et al. |
| 6,225,198 | B1 | 5/2001 | Alivisatos et al. |
| 8,105,393 | B2 | 1/2012 | Suddaby et al. |
| 2004/0170588 | A1 | 9/2004 | Bara et al. |
| 2005/0063933 | A1 | 3/2005 | Vrignaud et al. |

(Continued)

FOREIGN PATENT DOCUMENTS

| | | | |
|---|---|---|---|
| EP | 0186507 | A2 | 7/1986 |
| EP | 0342834 | A2 | 11/1989 |

(Continued)

OTHER PUBLICATIONS

Schlosser (J Cosmet Sci. 2004:55 Suppl:S123-31).*
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Davies, J.T., "A Quantitative Kenetic Theory of Emulsion Type. I. Physical Chemistry of the Emulsifying Agent," Reprinted from: Gas/Liquid and Liquid/Liquid Interfaces, Proceedings of 2nd International Congress Surfact Activity, Butterworths, London, 1957, pp. 426-438.
Godfrey, K.M., "Cationic Emulsifiers in Cosmetics," J. Soc. Cosmetic Chemists, 17, (1966), pp. 17-27.
Griffin, William C., "Calculation of HLB Values of Non-Ionic Surfactants," J. Soc. Cosmet. Chemists, vol. 5 (1954), pp. 249-256.

(Continued)

*Primary Examiner* — Bong-Sook Baek
(74) *Attorney, Agent, or Firm* — THE MARBURY LAW GROUP, PLLC

(57) ABSTRACT

The subject of the present invention relates to a composition for dyeing keratin fibers, comprising: a) one or more copolymer(s) derived from the polymerization of at least one monomer of crotonic acid or crotonic acid derivative and of at least one vinyl ester monomer, b) at least one oil-in-water emulsion having a particle size D 50 of less than 350 nm and which comprises: a silicone mixture comprising (i) at least one polydialkylsiloxane comprising trialkylsilyl end groups, having a viscosity at 25° C. ranging from 40 000 to 100 000 mPa·s and (ii) at least one aminosilicone having a viscosity at 25° C. ranging from 1000 to 15 000 mPa·s and an amine number ranging from 2 to 10 mg of KOH per gram of aminosilicone; a surfactant mixture comprising one or more nonionic surfactants, said mixture having an HLB ranging from 10 to 16, and water and c) at least one pigment.

10 Claims, No Drawings

(56) References Cited

U.S. PATENT DOCUMENTS

| | | | |
|---|---|---|---|
| 2005/0226838 A1* | 10/2005 | Krause | A61Q 5/12 424/70.13 |
| 2007/0224145 A1 | 9/2007 | Walter et al. | |
| 2013/0149358 A1 | 6/2013 | Colaco | |
| 2013/0164248 A1 | 6/2013 | Khenniche | |
| 2016/0213598 A1 | 7/2016 | Oh et al. | |
| 2020/0163862 A1 | 5/2020 | Seneca et al. | |

FOREIGN PATENT DOCUMENTS

| | | | | |
|---|---|---|---|---|
| EP | 0530974 A1 | 3/1993 | | |
| EP | 0945130 A2 | 9/1999 | | |
| EP | 1184426 A2 | 3/2002 | | |
| FR | 1222944 A | 6/1960 | | |
| FR | 1564110 A | 4/1969 | | |
| FR | 1580545 A | 9/1969 | | |
| FR | 2265781 A1 | 10/1975 | | |
| FR | 2265782 A1 | 10/1975 | | |
| FR | 2416723 A1 | 9/1979 | | |
| FR | 2439798 A1 | 5/1980 | | |
| FR | 2679771 A1 | 2/1993 | | |
| FR | 2709418 A1 | 3/1995 | | |
| FR | 2741530 A1 | 5/1997 | | |
| FR | 2750601 A1 | 1/1998 | | |
| FR | 2758719 A1 | 7/1998 | | |
| GB | 922457 A | 4/1963 | | |
| JP | 05-017710 A | 1/1993 | | |
| JP | 07-258460 A | 10/1995 | | |
| JP | 09-188830 A | 7/1997 | | |
| JP | H10-502945 A | 3/1998 | | |
| JP | 10-158450 A | 6/1998 | | |
| JP | 10-158541 A | 6/1998 | | |
| JP | 2003-201217 A | 7/2003 | | |
| JP | 2007-511551 A | 5/2007 | | |
| WO | 2009/049746 A2 | 4/2009 | | |
| WO | 2017/108824 A1 | 6/2017 | | |
| WO | WO-2017109692 A1 * | 6/2017 | | A61K 8/062 |
| WO | 2018/206453 A1 | 11/2018 | | |
| WO | 2018/206456 A1 | 11/2018 | | |

OTHER PUBLICATIONS

Mintel, "Cover Hair Root Retouch Concealer Spray," CCD Cosmetica Cientifica Dermatologica, XP002776566, Dec. 2016.

Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.

Puisieux, F., et al., Galencia 5: Les systèmes dispersés—Tome 1—Agents de surface et emulsions—Chapitre IV—Notions de HLB et du HLB critique, pp. 153-194—paragraph 1.1.2 Détermination de HLB par voie expérimental [Experimental determination of HLB], pp. 164-180.

Mintel, "Hair Spray," Baston do Brasil Produtos Quimicos, XP002773537, Sep. 2016.

Todd, Charles, et al., "Volatile Silicone Fluids for Cosmetic Formulations," Cosmetics and Toiletries, vol. 91, Jan. 1976, pp. 29-32.

International Search Report and Written Opinion for counterpart Application No. PCT/EP2018/61575, dated Jun. 20, 2018.

International Search Report and Written Opinion for counterpart Application No. PCT/EP2018/061581, dated Jul. 2, 2018.

International Search Report and Written Opinion for counterpart Application No. PCT/EP2018/066801, dated Aug. 16, 2018.

Non-Final Office Action for copending U.S. Appl. No. 16/611,825, mailed Mar. 10, 2021.

Final Office Action for copending U.S. Appl. No. 16/611,787, mailed Mar. 23, 2021.

Translated Notice of Reasons for Refusal for counterpart Japanese Application No. 2019-555650, dated Oct. 12, 2020.

Translated Notice of Reasons for Refusal for counterpart Japanese Application No. 2020-503366, dated Nov. 2, 2020.

1 Non-Final Office Action for copending U.S. Appl. No. 16/611,825, mailed Jul. 2, 2020.

Non-Final Office Action for copending U.S. Appl. No. 16/611,787, dated Sep. 9, 2021.

"Direct Dye," Britannica Online Encyclopedia, Jul. 20, 1998.

Non-Final Office Action for copending U.S. Appl. No. 16/611,787, mailed Sep. 25, 2020.

Translation of Japanese Office Action for counterpart Application No. 201880042314.4, dated Feb. 9, 2022.

Translation of Chinese Office Action for counterpart Application No. 201880042314.4, dated Feb. 9, 2022.

* cited by examiner

DYE COMPOSITION BASED ON COPOLYMERS DERIVED FROM THE POLYMERIZATION OF AT LEAST ONE CROTONIC ACID MONOMER OR CROTONIC ACID DERIVATIVE AND ON SILICONE

CROSS REFERENCE TO RELATED APPLICATION

This is a national stage application of PCT/EP2018/066801, filed internationally on Jun. 22, 2018, which claims priority to French Application No. 1756128, filed on Jun. 30, 2017, both of which are incorporated by reference herein in their entireties.

The subject of the present invention is a composition for dyeing keratin fibers, comprising at least one copolymer derived from the polymerization of at least one monomer of crotonic acid or crotonic acid derivative and of at least one vinyl ester monomer, at least one specific oil-in-water emulsion comprising silicones and at least one pigment, and also a dyeing process using said composition.

In the field of dyeing keratin fibers, in particular human keratin fibers, it is already known practice to dye keratin fibers via various techniques using direct dyes or pigments for non-permanent dyeing, or dye precursors for permanent dyeing.

There are essentially three types of process for dyeing the hair:
a) "permanent" dyeing, the function of which is to afford a substantial modification to the natural color and which uses oxidation dyes which penetrate into the hair fiber and forms the dye via an oxidative condensation process;
b) non-permanent, semi-permanent or direct dyeing, which does not use the oxidative condensation process and withstands four or five shampoo washes; it consists in dyeing keratin fibers with dye compositions containing direct dyes. These dyes are colored and coloring molecules that have affinity for keratin fibers,
c) temporary dyeing, which gives rise to a modification of the natural color of the hair that remains from one shampoo washing to the next, and which serves to enhance or correct a shade that has already been obtained. It may also be likened to a "makeup" process.

For this last type of dyeing, it is known practice to use colored polymers formed by grafting one or more dyes of azo, triphenylmethane, azine, indoamine or anthraquinone nature onto a polymer chain. These colored polymers are not entirely satisfactory, especially as regards the homogeneity of the coloring obtained and its resistance, not to mention the problems associated with their manufacture and especially with their reproducibility.

Another dyeing method consists in using pigments. Specifically, the use of pigment on the surface of keratin fibers generally makes it possible to obtain visible colorings on dark hair, since the surface pigment masks the natural color of the fiber. The use of pigment for dyeing keratin fibers is described, for example, in patent application FR 2 741 530; when they are applied to keratin fibers, these compositions have the drawback of transferring, i.e. of becoming at least partly deposited, leaving marks, on certain supports with which they may be placed in contact and in particular clothing or the skin. This results in mediocre persistence of the applied film, making it necessary to regularly repeat the application of the composition. Moreover, the appearance of these unacceptable marks may put certain people off using this type of dyeing.

Compositions for temporarily dyeing and/or making up the hair may also lead to a hair feel that is uncosmetic and/or not natural; the hair thus dyed may in particular lack softness and/or suppleness and/or individualization.

There is thus still a need to obtain compositions for the temporary dyeing of keratin materials, especially the hair, which have the advantage of forming a transfer-resistant deposit, which in particular does not become deposited, at least partly, onto supports with which said compositions are placed in contact, such as the skin (in particular the hands and the face) and/or clothing.

The invention is directed toward providing compositions which do not degrade keratin fibers, which do not impair their cosmetic properties such as softness and suppleness, keep the hair strands clearly individualized with no coarse feel, while at the same time having transfer-resistance properties.

This objective is achieved with the present invention, one subject of which is a composition for dyeing keratin fibers, especially human keratin fibers such as the hair, comprising:
a) at least one copolymer derived from the polymerization of at least one monomer of crotonic acid or crotonic acid derivative and of at least one vinyl ester monomer,
b) at least one oil-in-water emulsion having a particle size $D_{50}$ of less than 350 nm and which comprises:
  a silicone mixture comprising (i) at least one polydialkylsiloxane comprising trialkylsilyl end groups, having a viscosity at 25° C. ranging from 40 000 to 100 000 mPa·s and (ii) at least one aminosilicone having a viscosity at 25° C. ranging from 1000 to 15 000 mPa·s and an amine number ranging from 2 to 10 mg of KOH per gram of aminosilicone;
  a surfactant mixture comprising one or more nonionic surfactants, said mixture having an HLB ranging from 10 to 16, and
  water and
c) at least one pigment.

A subject of the invention is also a process for dyeing keratin fibers, especially human keratin fibers such as the hair, comprising the application to said fibers of a composition as defined above.

The term "at least one" means "one or more".

The term "comprising a" means "comprising at least one", unless otherwise specified.

The composition according to the invention is preferably a cosmetic composition, preferably for dyeing keratin fibers, in particular human keratin fibers such as the hair.

It has been observed that by using the dye composition according to the invention, it is possible to improve the individualization of the hair strands, and also to reduce the transfer. The fibers also have a smoother feel, are softer and more supple, and disentangle more easily.

a) Crotonic Acid Copolymers

The composition according to the invention comprises at least one copolymer derived from the polymerization of at least one monomer of crotonic acid or crotonic acid derivative and of at least one vinyl ester monomer, preferably at least two different vinyl ester monomers.

Preferably, the copolymer according to the invention is chosen from copolymers derived from the polymerization of at least one crotonic acid monomer and of at least one vinyl ester monomer, preferably at least two different vinyl ester monomers.

The term "crotonic acid derivative" preferably means a crotonic acid ester or a crotonic acid amide.

The term "crotonic acid derivative" preferably means a crotonic acid ester or amide, in particular:
(i) the crotonic acid esters of formula $CH_3CH=CHCOOR'1$ with R'1 representing a linear, branched or cyclic, saturated or unsaturated, optionally aromatic (aryl, aralkyl or alkylaryl) carbon-based and especially hydrocarbon-based (alkyl) chain, containing 1 to 30 carbon atoms, optionally comprising one or more functions chosen from —OH, —OR' with R' C1-C6 alkyl (alkoxy), —CN, —X (halogen, especially Cl, F, Br or I); mention may be made, for example, of methyl crotonoate and ethyl crotonoate,
(ii) the crotonic acid amides of formula $CH_3CH=CHCONR'2R''2$ with R'2 and R''2, which may be identical or different, representing hydrogen or a linear, branched or cyclic, saturated or unsaturated, optionally aromatic, carbon-based and especially hydrocarbon-based (alkyl) chain, containing 1 to 30 carbon atoms, optionally comprising one or more functions chosen from —OH, —OR' with R' C1-C6 alkyl (alkoxy), —CN, —X (halogen, especially Cl, F, Br or I).

The term "crotonic acid derivative" preferably means a crotonic acid ester or amide, in particular:
(i) the crotonic acid esters of formula $CH_3CH=CHCOOR'1$ with R'1 representing a linear, branched or cyclic, saturated or unsaturated, optionally aromatic such as an aryl, aralkyl or alkylaryl, carbon-based and especially hydrocarbon-based chain such as an alkyl, containing 1 to 30 carbon atoms, optionally comprising one or more functions chosen from —OH, —OR' with R'C1-C6 alkyl such as an alkoxy, —CN, —X such as a halogen, especially Cl, F, Br or I; mention may be made, for example, of methyl crotonoate and ethyl crotonoate,
(ii) the crotonic acid amides of formula $CH_3CH=CHCONR'2R''2$ with R'2 and R''2, which may be identical or different, representing hydrogen or a linear, branched or cyclic, saturated or unsaturated, optionally aromatic, carbon-based and especially hydrocarbon-based chain such as an alkyl, containing 1 to 30 carbon atoms, optionally comprising one or more functions chosen from —OH, —OR' with R' $C_1$-$C_6$ alkyl such as an alkoxy, —CN, —X such as a halogen, especially Cl, F, Br or I.

The vinyl ester monomer(s) may be chosen from the compounds of formula $CH_2=CH-OCO-R'3$ with R'3 representing a linear, branched or cyclic, saturated or unsaturated, optionally aromatic, carbon-based and especially hydrocarbon-based chain, containing 1 to 30 carbon atoms, optionally comprising one or more functions chosen from —OH, —OR' with R' $C_1$-$C_6$ alkyl (alkoxy), —CN, —X (halogen, especially Cl, F, Br or I).

Mention may be made especially of vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate and vinyl trifluoroacetate.

Preferably, the copolymer according to the invention is chosen from copolymers derived from the polymerization of at least one crotonic acid monomer and of at least two different vinyl ester monomers, said vinyl ester monomers preferably being chosen from vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate and vinyl trifluoroacetate, preferably from vinyl acetate, vinyl propionate and vinyl neodecanoate, better still from vinyl acetate and vinyl neodecanoate.

More particularly, the copolymer according to the invention is chosen from copolymers derived from the polymerization of crotonic acid, vinyl acetate and vinyl propionate, copolymers derived from the polymerization of crotonic acid, vinyl acetate and vinyl neodecanoate, and mixtures thereof.

According to a particular embodiment, the copolymer of the composition according to the invention is a crotonic acid/vinyl acetate/vinyl neodecanoate terpolymer.

The copolymers according to the invention may optionally comprise other monomers such as allylic or methallylic esters, or vinyl ethers. These polymers may optionally be grafted or crosslinked.

Such polymers are described, inter alia, in French patent Nos. 1 222 944, 1 580 545, 2 265 782, 2 265 781, 1 564 110 and 2 439 798. Commercial products which fall into this category are the products Resyn® 28-2930 and 28-1310 sold by the company Akzo Nobel (INCI names VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name VA/crotonates copolymer) and Mexomere® PW or PAM sold by the company Chimex (INCI name VA/vinyl butyl benzoate/crotonates copolymer).

The total amount of copolymer(s) of crotonic acid or crotonic acid derivative according to the invention may range from 0.05% to 15% by weight relative to the weight of the composition, preferably from 0.1% to 10% by weight relative to the weight of the composition, preferably from 1% to 5% by weight relative to the weight of the composition.

b) Silicone Emulsion (Oil-In-Water Emulsion)

The composition according to the invention also comprises an oil-in-water emulsion having a particle size D50 of less than 350 nm, and comprising:
- a silicone mixture comprising (i) at least one polydialkylsiloxane comprising trialkylsilyl end groups, having a viscosity at 25° C. ranging from 40 000 to 100 000 mPa·s and (ii) at least one aminosilicone having a viscosity at 25° C. ranging from 1000 to 15 000 mPa·s and an amine number ranging from 2 to 10 mg of KOH per gram of aminosilicone;
- a surfactant mixture comprising one or more nonionic surfactants, said mixture having an HLB ranging from 10 to 16, and
- water.

In the oil-in-water, or silicone-in-water, emulsion according to the invention, a liquid phase (the dispersed phase) is advantageously dispersed in another liquid phase (the continuous phase); in the present invention, the mixture of silicones, or silicone phase, is dispersed in the aqueous continuous phase.

The mixture of silicones (or silicone mixture) comprises one or more polydialkylsiloxanes comprising trialkylsilyl end groups, preferably of formula (I): R'3SiO(R'2SiO)pSiR'3 in which:
R', which may be identical or different, is a monovalent hydrocarbon-based radical having from 1 to 18 carbon atoms, preferably from 1 to 6 carbon atoms, better still from 1 to 3 carbon atoms, even better still a methyl radical, and p is an integer ranging from 500 to 2000, better still from 1000 to 2000.

The polydialkylsiloxanes comprising trialkylsilyl end groups according to the invention have a viscosity ranging from 40 000 to 100 000 mPa·s (preferably 100 000 excluded) at 25° C., preferably ranging from 40 000 to 70 000 mPa·s at 25° C., better still from 51 000 to 70 000 mPa·s at 25° C.

The polydialkylsiloxanes comprising trialkylsilyl end groups according to the invention are preferably linear, but they may comprise, in addition to the R'2SiO$_{2/2}$ units (D-units), additional RSiO$_{3/2}$ units (T-units) and/or SiO$_{4/2}$ units (Q-units), in which R', which may be identical or different, is a C1-C18 monovalent hydrocarbon-based radical.

Preferably, in formula (I), R', which may be identical or different, is:
- an alkyl, preferably $C_1$-$C_{28}$ alkyl, radical, such as the radicals methyl, ethyl, n-propyl, isopropyl, 1-n-butyl, 2-n-butyl, isobutyl, tert-butyl, n-pentyl, isopentyl, neopentyl, tert-pentyl, hexyl and in particular n-hexyl, heptyl and in particular n-heptyl, octyl and in particular n-octyl, isooctyl, 2,2,4-trimethylpentyl; nonyl and in particular n-nonyl; decyl and in particular n-decyl; dodecyl and in particular n-dodecyl; octadecyl and in particular n-octadecyl;
- an alkenyl radical such as vinyl and allyl;
- a cycloalkyl radical such as cyclopentyl, cyclohexyl, cycloheptyl and methylcyclohexyl;
- an aryl radical such as phenyl, naphthyl, anthryl and phenanthryl;
- an alkaryl radical such as the radicals o-, m- and p-tolyl; xylyl, ethylphenyl;
- an aralkyl radical such as benzyl and phenylethyl.

Preferentially, R' is a methyl radical.

Preferably, the polydialkylsiloxanes comprising trialkylsilyl end groups are polydimethylsiloxanes (PDMSs) comprising trialkylsilyl end groups.

The silicone mixture also comprises one or more aminosilicones, preferably of formula (II): $XR_2Si(OSiAR)_n(OSiR_2)_mOSiR_2X$ in which:
- R, which may be identical or different, is a monovalent hydrocarbon-based radical having from 1 to 18 carbon atoms, preferably from 1 to 6 carbon atoms, better still from 1 to 3 carbon atoms, even better still a methyl radical,
- X, which may be identical or different, represents R or a hydroxyl (OH) or a $C_1$-$C_6$ alkoxy group; preferably X is R, that is to say a monovalent hydrocarbon-based radical having from 1 to 18 carbon atoms, preferably from 1 to 6 carbon atoms, better still from 1 to 3 carbon atoms, even better still a methyl radical,
- A is an amino radical of formula —R$^1$—[NR$^2$—R$^3$—]$_x$NR$^2$$_2$, or the protonated form of this amino radical, with
  - R$^1$ representing a $C_1$-$C_6$ alkylene radical, preferably a —CH$_2$CH$_2$CH$_2$— or —CH$_2$CH(CH$_3$)CH$_2$— radical,
  - R$^2$, which may be identical or different, being a hydrogen atom or a $C_1$-$C_4$ alkyl radical, preferably a hydrogen atom,
  - R$^3$ being a $C_1$-$C_6$ alkylene radical, preferably a —CH$_2$CH$_2$— radical,
  - x being 0 or 1;
- m and n are integers such that m+n ranges from 50 to 1000, better still from 50 to 600.

Preferably, A is an amino radical of formula —R$^1$—[NR$^2$—R$^3$—]$_x$NR$^2$$_2$, or the protonated form of this amino radical, with R$^1$ being —CH$_2$CH$_2$CH$_2$— or —CH$_2$CH(CH$_3$)CH$_2$—, R$^2$ being hydrogen atoms, R$^3$ being —CH$_2$CH$_2$— and x being equal to 1.

Preferably, R, which may be identical or different, is:
- an alkyl, preferably C1-C28 alkyl, radical, such as the radicals methyl, ethyl, n-propyl, isopropyl, 1-n-butyl, 2-n-butyl, isobutyl, tert-butyl, n-pentyl, isopentyl, neopentyl, tert-pentyl, hexyl and in particular n-hexyl, heptyl and in particular n-heptyl, octyl and in particular n-octyl, isooctyl, 2,2,4-trimethylpentyl; nonyl and in particular n-nonyl; decyl and in particular n-decyl; dodecyl and in particular n-dodecyl; octadecyl and in particular n-octadecyl;
- an alkenyl radical such as vinyl and allyl;
- a cycloalkyl radical such as cyclopentyl, cyclohexyl, cycloheptyl and methylcyclohexyl;
- an aryl radical such as phenyl, naphthyl, anthryl and phenanthryl;
- an alkaryl radical such as the radicals o-, m- and p-tolyl; xylyl, ethylphenyl;
- an aralkyl radical such as benzyl and phenylethyl.

Preferentially, R is a methyl radical.

The aminosilicones according to the invention have a viscosity, at 25° C., ranging from 1000 to 15 000 mPa·s, preferably from 1500 to 15 000 mPa·s.

The aminosilicones according to the invention have an amine number ranging from 2 to 10 mg of KOH per gram of aminosilicone; preferably from 3.5 to 8 mg.

The molar percentage of amine function is preferably between 0.3 and 8 mol %.

As examples of aminosilicones, mention may be made of aminosilicones comprising trialkylsilyl end groups; preferably aminoethylaminopropylmethylsiloxanes comprising trialkylsilyl end groups, even better still copolymers of aminoethylaminopropylmethylsiloxane comprising trialkylsilyl end groups/dimethylsiloxane.

The amino radical A may be partially or totally protonated, for example by addition of acids to the aminosilicone, so as to obtain the salified form of said amino radical.

As acids that may be used, mention may be made of linear or branched carboxylic acids having from 3 to 18 carbon atoms, such as formic acid, acetic acid, propionic acid, butyric acid, pivalic acid, sorbic acid, benzoic acid or salicylic acid. Preferably, the acids may be used in a proportion of from 0.1 to 2.0 mol per mole of amino radical A in the amino silicone of formula (II).

The silicone mixture preferably comprises (i) one or more polydialkylsiloxanes comprising trialkylsilyl end groups, having a viscosity, at 25° C., ranging from 40 000 to 100 000 mPa·s, in an amount of from 70% to 90% by weight, preferably from 75% to 85% by weight, and (ii) one or more aminosilicones having a viscosity, at 25° C., ranging from 1000 to 15 000 mPa·s and an amine number ranging from 2 to 10 mg of KOH per gram of aminosilicone, in an amount of from 10% to 30% by weight, in particular from 15% to 25% by weight, relative to the total weight of the silicone mixture.

The oil-in-water emulsion also comprises a surfactant mixture which comprises one or more nonionic surfactants; said surfactant mixture may optionally comprise one or more cationic surfactants.

Said surfactant mixture has an HLB ranging from 10 to 16.

The nonionic surfactants that may be used may be chosen from alcohols, α-diols and $(C_{1-20})$alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or else these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl) aminopropylmorpholine oxides.

Mention may also be made of nonionic surfactants of alkyl(poly)glycoside type, represented especially by the following general formula: $R_1O$—$(R_2O)_t$-$(G)_v$ in which:
  $R_1$ represents a linear or branched alkyl or alkenyl radical comprising 6 to 24 carbon atoms and especially 8 to 18 carbon atoms, or an alkylphenyl radical of which the linear or branched alkyl radical comprises 6 to 24 carbon atoms and especially 8 to 18 carbon atoms;
  $R_2$ represents an alkylene radical comprising 2 to 4 carbon atoms,
  G represents a sugar unit comprising 5 to 6 carbon atoms,
  t denotes a value ranging from 0 to 10 and preferably from 0 to 4,
  v denotes a value ranging from 1 to 15 and preferably from 1 to 4.

Preferably, the alkyl(poly)glycoside surfactants are compounds of the formula described above in which:
  $R_1$ denotes a linear or branched, saturated or unsaturated alkyl radical comprising from 8 to 18 carbon atoms,
  $R_2$ represents an alkylene radical comprising 2 to 4 carbon atoms,
  t denotes a value ranging from 0 to 3 and preferably equal to 0,
  G denotes glucose, fructose or galactose, preferably glucose;
  the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$ alkyl(poly)glucosides 1,4, and in particular decyl glucosides and caprylyl/capryl glucosides, are most particularly preferred.

Among commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or else the products sold by the company Chem Y under the name AG10 LK.

Preferably, use is made of $C_8/C_{16}$ alkyl(poly)glycosides 1,4, in particular as an aqueous 53% solution, such as those sold by Cognis under the reference Plantacare® 818 UP.

The mono- or polyglycerolated surfactants preferably comprise an average number of glycerol groups ranging from 1 to 30, in particular from 1 to 10, better still from 1.5 to 5. They preferably correspond to one of the following formulae:

RO[CH$_2$CH(CH$_2$OH)O]mH,

RO[CH$_2$CH(OH)CH$_2$O]mH or

RO[CH(CH$_2$OH)CH$_2$O]mH;

in which:
  R represents a saturated or unsaturated, linear or branched hydrocarbon-based (in particular alkyl or alkenyl) radical comprising 8 to 40 carbon atoms, in particular 10 to 30 carbon atoms, optionally comprising one or more heteroatoms such as O and N; and
  m is an integer ranging from 1 to 30, preferably from 1 to 10, better still from 1.5 to 6.

In particular, R may comprise one or more hydroxyl and/or ether and/or amide groups. Preferably, R is a mono- or polyhydroxylated $C_{10}$-$C_{20}$ alkyl or alkenyl radical.

Mention may be made of polyglycerolated (3.5 mol) hydroxylauryl ether, such as the product Chimexane® NF from Chimex.

Mention may also be made of (poly)ethoxylated fatty alcohols preferably comprising one or more saturated or unsaturated, linear or branched hydrocarbon-based chains comprising 8 to 30 carbon atoms, preferably from 12 to 22 carbon atoms, optionally substituted with one or more hydroxyl (OH) groups, in particular 1 to 4 hydroxyl groups.

When the chain is unsaturated, it may comprise one to three conjugated or non-conjugated carbon-carbon double bonds.

The (poly)ethoxylated fatty alcohols preferably correspond to formula (II):

R3-(OCH$_2$CH$_2$)cOH in which:
  R3 represents a linear or branched alkyl or alkenyl radical comprising from 8 to 40 carbon atoms and in particular 8 to 30 carbon atoms, optionally substituted with one or more, in particular 1 to 4, hydroxyl groups; and
  c is an integer ranging from 1 to 200, in particular from 2 to 150, or even from 4 to 50 and even better still from 8 to 30.

The (poly)ethoxylated fatty alcohols are more particularly fatty alcohols comprising from 8 to 22 carbon atoms, oxyethylenated with 1 to 30 mol of ethylene oxide (1 to 30 EO); mention may in particular be made of lauryl alcohol 2 EO; lauryl alcohol 3 EO; decyl alcohol 3 EO; decyl alcohol 5 EO and oleyl alcohol 20 EO.

The nonionic surfactants may advantageously be chosen from:
(i) (poly)oxyalkylenated, in particular (poly)ethoxylated, fatty alcohols, and in particular those of formula: $R_3$—(OCH$_2$CH$_2$)cOH in which:
  R3 represents a linear or branched alkyl or alkenyl radical comprising from 8 to 40 carbon atoms and in particular 8 to 30 carbon atoms, optionally substituted with one or more, in particular 1 to 4, hydroxyl groups; and
  c is an integer ranging from 1 to 200, in particular from 2 to 150, or even from 4 to 50 and even better still from 8 to 20;

(ii) (poly)oxyalkylenated ($C_8$-$C_{32}$)alkyl phenyl ethers, in particular comprising from 1 to 200, better still from 1 to 30 mol of ethylene oxide;

(iii) polyoxyalkylenated esters of $C_8$-$C_{32}$ fatty acids and of sorbitan, in particular polyoxyethylenated esters of $C_8$-$C_{32}$ fatty acids and of sorbitan, preferably having from 2 to 40 ethylene oxide units, better still from 2 to 20 ethylene oxide (EO) units; in particular polyoxyethylenated esters of $C_{10}$-$C_{24}$ fatty acids and of sorbitan, preferably having from 2 to 40 ethylene oxide units, better still from 2 to 20 ethylene oxide (EO) units; and (iv) polyoxyethylenated esters of $C_8$-$C_{32}$ fatty acids, preferably having from 2 to 150 ethylene oxide units; in particular polyoxyethylenated esters of $C_{10}$-$C_{24}$ fatty acids, comprising in particular 2 to 150 ethylene oxide (EO) units.

The nonionic surfactants may advantageously be chosen from alkyl ethers and alkyl esters of polyalkylene glycol, in particular of polyethylene glycol.

Mention may in particular be made of:

polyethylene glycol octyl ether; polyethylene glycol lauryl ether; polyethylene glycol tridecyl ether; polyethylene glycol cetyl ether; polyethylene glycol stearyl ether; and most particularly trideceth-3, trideceth-10 and steareth-6;

polyethylene glycol nonylphenyl ether; polyethylene glycol dodecylphenyl ether; polyethylene glycol cetylphenyl ether; polyethylene glycol stearylphenyl ether;

polyethylene glycol sorbitan monostearate, polyethylene glycol sorbitan monooleate;

polyethylene glycol stearate, and in particular PEG100 stearate.

Even better still, the nonionic surfactants may be chosen from Steareth-6, PEG100 stearate, trideceth-3 and trideceth-10, and mixtures thereof; most particularly, a mixture comprising these four nonionic surfactants.

The surfactant mixture may optionally comprise one or more cationic surfactants, which may be chosen from tetraalkylammonium, tetraarylammonium and tetraalkylarylammonium salts, in particular halides, and most particularly from cetrimonium or behentrimonium salts, in particular halides, better still chlorides.

The oil-in-water emulsion preferably comprises the surfactant mixture in a total amount ranging from 5% to 15% by weight, in particular from 8% to 15% by weight, even better still from 10% to 12% by weight, relative to the total weight of the emulsion.

The oil-in-water emulsion preferably comprises the nonionic surfactant(s) in a total amount ranging from 5% to 15% by weight, in particular from 8% to 15% by weight, even better still from 10% to 12% by weight, relative to the total weight of the emulsion.

The oil-in-water emulsion preferably comprises the cationic surfactant(s), when they are present, in a total amount ranging from 0.5% to 1.5% by weight relative to the total weight of the emulsion.

The oil-in-water emulsion preferably comprises the silicone mixture in a total amount ranging from 40% to 60% by weight, in particular from 45% to 55% by weight, relative to the total weight of the emulsion.

The oil-in-water emulsion preferably comprises the polydialkylsiloxane(s) comprising trialkylsilyl end groups in a total amount ranging from 35% to 45% by weight, in particular from 38% to 42% by weight, relative to the total weight of the emulsion.

The oil-in-water emulsion preferably comprises the aminosilicone(s) in a total amount ranging from 5% to 15% by weight, in particular from 8% to 12% by weight, relative to the total weight of the emulsion.

The oil-in-water emulsion preferably comprises water in a total amount ranging from 25% to 50% by weight, in particular from 30% to 45% by weight, even better still from 35% to 42% by weight, relative to the total weight of the emulsion.

The oil-in-water emulsion may also comprise a preservative, such as phenoxyethanol, in an amount ranging from 0.5% to 1% by weight relative to the total weight of the emulsion.

A process for preparing the oil-in-water emulsion preferably comprises:

a step of mixing one or more polydialkylsiloxanes comprising trialkylsilyl end groups, having a viscosity, at 25° C., ranging from 40 000 to 100 000 mPa·s, and one or more aminosilicones having a viscosity, at 25° C., ranging from 1000 to 15 000 mPa·s and an amine number ranging from 2 to 10 mg of KOH per gram of aminosilicone; at a temperature of from 15° C. to 40° C., in particular at 25° C., in order to obtain a fluid mixture of silicones; then a step of adding a surfactant mixture comprising one or more nonionic surfactants, said mixture having an HLB ranging from 10 to 16, to said fluid mixture of silicones, in order to obtain an emulsified silicone mixture; then a step of homogenizing said emulsified silicone mixture, followed by a step of adding water, in particular demineralized water, preferentially in steps, in order to obtain an oil-in-water emulsion having a particle size D50 of less than 350 nm.

The preparation process may also comprise an additional step of adding one or more preservatives.

The pH of the oil-in-water emulsion is generally between 4 and 6.

The oil-in-water emulsion has a particle size D50 of less than 350 nm, in particular of between 100 and 300 nm, better still between 150 and 250 nm, or even between 160 and 200 nm.

This size corresponds to the average hydrodynamic particle diameter. The particle size D50 is expressed by volume. It can be measured using a ZetaSizer device from Malvern, UK, model Nano-ZS, based on the "Photon Correlation Spectroscopy (PCS)" method.

Method for Measuring the Particle Size

The particle size of the emulsion is measured using a ZetaSizer device from Malvern, UK, model Nano-ZS, based on the "Photon Correlation Spectroscopy (PCS)" method.

The particle size D50 is measured when the evaluation algorithm is "cumulant analysis".

0.5 g of the emulsion is placed in a 250 ml beaker, 100 ml of demineralized water are added and mixing is carried out in order to obtain the solution to be tested. The solution to be tested is placed in the measuring vessel (or cell) and introduced into the measuring device.

The size $D_{50}$ corresponds to the particle diameter value at 50% in cumulative distribution.

For example, if $D_{50}$=170 nm, this means that 50% of the particles have a size of greater than 170 nm, and that 50% of the particles have a size of less than 170 nm.

It should be recalled that this distribution is by volume.

Method for Measuring the Viscosity

The viscosities, in particular of the silicone compounds, are measured at 25° C., 1 atm.

To measure viscosities of between 1000 and 40 000 mPa·s at 25° C., use may be made of an Anton Paar rheometer, model MCR101, cylinder geometry, single gap: CC27 spindle, shear rate 1 s$^{-1}$ for 2 minutes, at 25° C.

To measure viscosities of between 40 000 and 100 000 mPa·s at 25° C., use may be made of an Anton Paar rheometer, model MCR101, 25-6 cone (cone-plate geometry, 25 mm in diameter/6° cone); Zero gap, shear rate 1 s$^{-1}$ for 2 minutes, at 25° C.

Three measurements are carried out for each sample, and the viscosity value is taken at 60 seconds. The MCR Rheometer Series products operate according to the USP convention (US Pharmacopeia Convention, 912—Rotational Rheometer methods).

Method for Measuring the Amine Number

The amine number can be measured by acid-base titration, using a potentiometer [Make: Veego; model VPT-MG].

0.6 g of the sample is placed in a 500 ml beaker and a 1:1 toluene-butanol mixture is added, then mixing is carried out.

The solution is titrated with a 0.1 N HCl solution. A determination of the zero value ($V_{blank}$) is also carried out with the 1:1 toluene-butanol mixture alone.

The amine number is calculated by means of the formula:

$$56.11 \times (V - V_{Blank}) \times N/W \text{ mg KOH/g of sample}$$

with V=volume of HCl required (in ml), $V_{Blank}$=volume of HCl required for the zero value (in ml); N=normality of HCl, i.e. 0.1, and W=weight of the sample (in g).

HLB Values

The term HLB relates to the hydrophilic-lipophilic balance of a surfactant. It can be measured experimentally or calculated.

In the present application, the HLB values are the values at 25° C.

The HLB values can be calculated by means of the following equation: HLB=(E+P)/5, in which E is the % by weight of oxyethylene and P is the % by weight of polyol, as is described in the publication Griffin, J. Soc. Cosm. Chem. 1954 (vol.5, No. 4), pages 249-256.

The HLB values can also be determined experimentally according to the book by Puisieux and Seiller, entitled "Galenica 5: Les systèmes disperses [Galenics 5: Dispersed systems]—Volume I—Agents de surface et émulsions [Surface agents and emulsions]—Chapter IV—Notions de HLB et de HLB critique [Notions of HLB and of critical HLB], pages 153-194—paragraph 1.1.2. Détermination de HLB par voie expérimentale [Experimental determination of HLB], pages 164-180".

Preferably, the HLB values that will be taken into account are those obtained by calculation, in particular in the following way: "calculated HLB"=20×(molar mass of the hydrophilic part/total molar mass).

Thus, for an oxyethylenated fatty alcohol, the hydrophilic part corresponds to the oxyethylene units fused to the fatty alcohol and the "calculated HLB" then corresponds to the "HLB according to Griffin".

For an ester or an amide, the hydrophilic part is generally defined as being beyond the carbonyl group, starting from the fatty chain(s).

The HLB values of nonionic surfactants can also be calculated by means of the Davies formula, as described in Davies J T (1957), "A quantitative kinetic theory of emulsion type, I. Physical chemistry of the emulsifying agent", Gas/Liquid and Liquid/Liquid Interface (Proceedings of the International Congress of Surface Activity): 426-438.

According to this formula, the HLB value is obtained by adding the hydrophilic/hydrophobic contribution linked to the constituent groups in the surfactant:

HLB=(number of hydrophilic groups)−n(number of groups per $CH_2$ group)+7.

The HLB values of some cationic surfactants are given in Table IV, in "Cationic emulsifiers in cosmetics", GODFREY, J. Soc. Cosmetic Chemists (1966) 17, pages 17-27.

When two surfactants A and B, of known HLB values, are mixed, the $HLB_{Mix}$ corresponds to the HLB of the mixture and can be expressed by the following equation:

$$HLB_{Mix} = (W_A HLB_A + W_B HLB_B)/(W_A + W_B)$$

in which $W_A$ is the amount (weight) of the $1^{st}$ surfactant A and $W_B$ the amount of the $2^{nd}$ surfactant B, and $HLB_A$ and $HLB_B$ are the HLB values of the surfactant A and of the surfactant B.

The oil-in-water silicone emulsion is advantageously present in a total amount of at least 0.1%, preferably of at least 0.3%, more preferentially of at least 0.5%, more preferably of at least 1%, better still of at least 1.5% by weight, relative to the total weight of the composition.

Advantageously, the composition according to the invention may comprise the oil-in-water silicone emulsion in a total amount ranging from 0.1% to 15% by weight, preferably from 0.3% to 12% by weight, more preferentially from 0.5% to 10% by weight, more preferably from 1% to 8% by weight, yet more preferably from 1.5% to 5% by weight, relative to the total weight of the composition.

Preferably, the composition according to the invention comprises the oil-in-water silicone emulsion in a total amount ranging from 0.1% to 15% by weight, preferably from 0.3% to 12% by weight, more preferentially from 0.5% to 10% by weight, more preferably from 1% to 8% by weight, yet more preferably from 1.5% to 5% by weight, relative to the total weight of the composition, and the emulsion has a solids (or active material) content of silicone(s) of between 40% and 60% by weight, in particular 45% to 55% by weight, relative to the total weight of the emulsion.

Preferably, the weight ratio of the total amount of copolymer(s) of crotonic acid or crotonic acid derivative according to the invention to the total amount of oil-in-water silicone emulsion ranges from 0.1 to 10, more preferentially from 0.3 to 7 and at best from 0.5 to 5.

c) Pigments

The composition comprises one or more pigments.

The term "pigment" is understood to mean white or colored particles of any shape which are insoluble in the composition in which they are present.

The pigments that may be used are especially chosen from the organic and/or mineral pigments known in the art, especially those described in Kirk-Othmer's Encyclopedia of Chemical Technology and in Ullmann's Encyclopedia of Industrial Chemistry.

They may be natural, of natural origin, or not.

These pigments may be in pigment powder or paste form.

They may be coated or uncoated.

The pigments may be chosen, for example, from mineral pigments, organic pigments, lakes, pigments with special effects, such as nacres or glitter flakes, and mixtures thereof.

The pigment may be a mineral pigment. The term "mineral pigment" means any pigment that satisfies the definition in Ullmann's encyclopedia in the chapter on inorganic pigments. Mention may be made, among mineral pigments of use in the present invention, of ochres, such as red ochre (clay (in particular kaolinite) and iron hydroxide (for example hematite)), brown ochre (clay (in particular kaolinite) and limonite) or yellow ochre (clay (in particular kaolinite) and goethite); titanium dioxide, optionally surface-treated; zirconium or cerium oxides; zinc, (black, yellow or red) iron or chromium oxides; manganese violet, ultramarine blue, chromium hydrate and ferric blue; or metal powders, such as aluminum powder or copper powder.

Mention may also be made of alkaline earth metal carbonates (such as calcium carbonate or magnesium carbonate), silicon dioxide, quartz and any other compound used as inert filler in cosmetic compositions, provided that these compounds contribute color or whiteness to the composition under the conditions under which they are employed.

The pigment may be an organic pigment. The term "organic pigment" means any pigment that satisfies the definition in Ullmann's encyclopedia in the chapter on organic pigments.

The organic pigment may especially be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in the cosmetics field, provided that these compounds give the composition color or whiteness under the conditions under which they are used, for example guanine, which, according to the refractive index of the composition, is a pigment.

In particular, the white or colored organic pigments may be chosen from carmine, carbon black, aniline black, azo yellow, quinacridone, phthalocyanine blue, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

Examples that may also be mentioned include pigmentary pastes of organic pigments, such as the products sold by the company Hoechst under the names:
  Cosmenyl Yellow IOG: Pigment Yellow 3 (CI 11710);
  Cosmenyl Yellow G: Pigment Yellow 1 (CI 11680);
  Cosmenyl Orange GR: Pigment Orange 43 (CI 71105);
  Cosmenyl Red R: Pigment Red 4 (CI 12085);
  Carmine Cosmenyl FB: Pigment Red 5 (CI 12490);
  Cosmenyl Violet RL: Pigment Violet 23 (CI 51319);
  Cosmenyl Blue A2R: Pigment Blue 15.1 (CI 74160);
  Cosmenyl Green GG: Pigment Green 7 (CI 74260);
  Cosmenyl Black R: Pigment Black 7 (CI 77266).

The pigments in accordance with the invention may also be in the form of composite pigments, as described in patent EP 1 184 426. These composite pigments may be composed especially of particles comprising a mineral core, at least one binder, which provides for the attachment of the organic pigments to the core, and at least one organic pigment which at least partially covers the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate or calcium aluminum borosilicate and aluminum.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

Mention may be made, as examples of lakes, of the product known under the following name: D&C Red 7 (CI 15 850:1).

The pigment may also be a pigment with special effects. The term "pigments with special effects" means pigments that generally create a colored appearance (characterized by a certain shade, a certain vivacity and a certain level of luminance) that is non-uniform and that changes as a function of the conditions of observation (light, temperature, angles of observation, etc.). They thus contrast with colored pigments that afford a standard uniform opaque, semi-transparent or transparent shade.

Several types of pigment with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, colored nacreous pigments such as mica coated with titanium and iron oxides, mica coated with iron oxide, mica coated with titanium and especially with ferric blue or with chromium oxide, mica coated with titanium and with an organic pigment of the abovementioned type, and also nacreous pigments based on bismuth oxychloride. Nacreous pigments that may be mentioned include the Cellini nacres sold by Engelhard (mica-TiO2-lake), Prestige sold by Eckart (mica-TiO2), Prestige Bronze sold by Eckart (mica-Fe2O3), and Colorona sold by Merck (mica-TiO2-Fe2O3).

Mention may also be made of the gold-colored nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a coppery glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red nacres with a gold glint sold especially by the company Engelhard under the name Sunstone G012 (Gemtone); the pink nacres sold especially by the company Engelhard under the name Tan opale G005 (Gemtone); the black nacres with a gold glint sold especially by the company Engelhard under the name Nu antique bronze 240 AB (Timica), the blue nacres sold especially by the company Merck under the name Matte blue (17433) (Microna), the white nacres with a silvery glint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

It is also possible to envisage multilayer pigments based on synthetic substrates, such as alumina, silica, calcium sodium borosilicate, calcium aluminum borosilicate and aluminum.

The pigments with special effects may also be chosen from reflective particles, i.e. especially from particles of which the size, structure, especially the thickness of the layer(s) of which they are made and their physical and chemical nature, and surface state, allow them to reflect incident light. This reflection may, if appropriate, have an intensity sufficient to create, at the surface of the composition or mixture, when the latter is applied to the substrate to be made up, highlight points visible to the naked eye, that is to say more luminous points which contrast with their surroundings by appearing to sparkle.

The reflective particles may be selected so as not to significantly alter the coloring effect generated by the coloring agents with which they are combined, and more particularly so as to optimize this effect in terms of color rendition. They may more particularly have a yellow, pink, red, bronze, orange, brown, gold and/or coppery color or glint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described in particular in the documents JP-A-09188830, JP-A-10158450, JP-A-10158541, JP-A-07258460 and JP-A-05017710.

Mention may also be made, still by way of example of reflective particles comprising a mineral substrate coated with a layer of metal, of the particles comprising a borosilicate substrate coated with silver.

Particles comprising a glass substrate coated with silver, in the form of platelets, are sold under the name Microglass Metashine REFSX 2025 PS by Toyal. Particles with a glass substrate coated with nickel/chromium/molybdenum alloy are sold under the name Crystal Star GF 550 and GF 2525 by this same company.

Use may also be made of particles comprising a metal substrate, such as silver, aluminum, iron, chromium, nickel, molybdenum, gold, copper, zinc, tin, magnesium, steel, bronze or titanium, said substrate being coated with at least one layer of at least one metal oxide, such as titanium oxide, aluminum oxide, iron oxide, cerium oxide, chromium oxide, silicon oxides and mixtures thereof.

Examples that may be mentioned include aluminum powder, bronze powder or copper powder coated with SiO2 sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, irradiation with a wavelength of between 400 nm and 700 nm. These nanoparticles are known from the literature. In particular, they may be synthesized according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterization of a size series of highly luminescent nanocrystallites", Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pages 7019-7029.

The variety of pigments that may be used in the present invention makes it possible to obtain a wide range of colors, and also particular optical effects such as metallic effects or interference effects.

The size of the pigment used in the cosmetic composition according to the present invention is generally between 10 nm and 200 µm, preferably between 20 nm and 80 µm and more preferably between 30 nm and 50 µm.

The pigments may be dispersed in the product by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters and $C_8$ to $C_{20}$ fatty acid esters of polyols such as glycerol or diglycerol are used, such as poly(12-hydroxystearic) acid stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminum salts of fatty acids, for example aluminum stearate or laurate; metal alkoxides; polyethylene; (meth) acrylic polymers, for example polymethyl methacrylates; polymers and copolymers containing acrylate units; alkanolamines; silicone compounds, for example silicones, polydimethylsiloxanes; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigment.

Preferably, the surface treatments of the pigments are chosen from the following treatments:
- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a magnesium myristate treatment, for instance the MM surface treatment sold by LCW;
- an aluminum dimyristate treatment, such as the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrogenosiloxane/perfluoroalkyl phosphate treatment, for instance the FS01 surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- an acrylate copolymer treatment, for instance the APD surface treatment sold by Daito;
- a perfluoroalkyl phosphate/isopropyl titanium triisostearate treatment, for instance the PF+ITT surface treatment sold by Daito.

Preferably, the pigment is chosen from mineral or mixed mineral-organic pigments.

The amount of pigment(s) may range from 0.01% to 30% by weight, more particularly from 0.05% to 20% by weight, preferably from 0.1% to 15% by weight and preferably from 1% to 10% by weight relative to the total weight of the composition.

The composition of the invention may contain colored or coloring species other than the pigments according to the invention, such as direct dyes or dye precursors.

Thickener

According to a preferred embodiment, the composition according to the invention comprises at least one thickener, preferably chosen from natural polymers, carboxyvinyl polymers such as homopolymers or copolymers of acrylic and/or methacrylic acid and/or ester, which are preferably crosslinked, crosslinked thickening polyacrylamides and associative polymers comprising at least one hydrophilic unit and at least one fatty chain.

According to the present invention, the term "thickener" refers to a compound which, by its presence at a concentration of 0.05% by weight, increases the viscosity of a composition into which it is introduced by at least 20 cps, preferably by at least 50 cps, at ambient temperature (25° C.), at atmospheric pressure and at a shear rate of $1\ s^{-1}$ (the viscosity may be measured using a cone/plate viscometer, a Haake R600 rheometer or the like).

The thickener(s) may be chosen especially from carboxyvinyl polymers such as crosslinked acrylic acid homopolymers (carbomer) such as those sold under the name Carbopol by the company Goodrich, polyacrylates and polymethacrylates such as the products sold under the names Lubrajel or Norgel by the company Guardian or under the name Hispagel by the company Hispano Chimica; polyacrylamides such as the product sold under the name Sepigel 305 by the company SEPPIC; polysaccharides such as alginates, cellulose and derivatives thereof, especially carboxymethylcellulo se, hydroxymethylcellulose, hydroxypropylcellulose and microcrystalline cellulose; natural gums such as xanthan gum, guar gum, locust bean gum, acacia gum, scleroglucans, chitin and chitosan derivatives, carrageenans; or clays such as montmorillonite, bentones and magnesium aluminum silicates (Veegum).

According to a particular embodiment of the invention, the composition comprises at least one thickener chosen from crosslinked acrylic and/or methacrylic acid polymers.

According to a particular embodiment of the invention, the composition comprises at least one thickener chosen from crosslinked acrylic acid homopolymers (INCI name Carbomer).

The thickener may be present in the composition in a total content ranging from 0.01% to 10% by weight relative to the weight of the composition, preferably from 0.1% to 5% by weight relative to the weight of the composition, preferably from 0.4% to 2% by weight relative to the weight of the composition.

The composition according to the invention advantageously comprises water, which may preferably be present in a content ranging from 20% to 98% by weight relative to the weight of the composition.

Additives

The compositions may also comprise at least one agent commonly used in cosmetics, for example chosen from reducing agents, fatty substances other than silicones, organic solvents, softeners, antifoams, moisturizers, UV-screening agents, peptizers, so lubilizers, fragrances, anionic, cationic, nonionic or amphoteric surfactants, proteins and vitamins.

The above additives are generally present in an amount for each of them of between 0.01% and 20% by weight relative to the weight of the composition.

Needless to say, those skilled in the art will take care to choose this or these optional additive(s) so that the advantageous properties intrinsically attached to the formation of the sheathing in accordance with the invention are not, or not substantially, detrimentally affected.

Presentation Form

The composition according to the invention may especially be in the form of a suspension, a dispersion, a gel, an emulsion, especially an oil-in-water (O/W) or water-in-oil (W/O) emulsion, or a multiple emulsion (W/O/W or polyol/O/W or O/W/O), in the form of a cream, a mousse, a stick, a dispersion of vesicles, especially of ionic or nonionic lipids, or a two-phase or multi-phase lotion. Preferably, the composition is in the form of a gel.

Those skilled in the art may select the appropriate presentation form, and also the method for preparing it, on the basis of their general knowledge, taking into account first the nature of the constituents used, especially their solubility in the support, and secondly the application envisaged for the composition.

Organic Solvents

The composition according to the invention may comprise one or more organic solvents.

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

Preferably, the composition according to the invention comprises one or more organic solvents.

When they are present, the organic solvents are present in proportions preferably inclusively between 0.1% and 40% by weight approximately relative to the total weight of the dye composition, more preferentially between 1% and 30% by weight approximately and even more particularly inclusively between 5% and 25% by weight relative to the total weight of the composition.

Process

The composition described above may be used on wet or dry keratin fibers, and also on any type of fair or dark, natural or dyed, permanent-waved, bleached or relaxed keratin fibers.

The application to the fibers may be performed via any standard means, in particular using a comb, a fine brush, a coarse brush or with the fingers.

Preferably, if the fibers are dried, they are dried, in addition to a supply of heat, with a flow of air.

During drying, a mechanical action may be exerted on the locks, such as combing, brushing or running the fingers through. This operation may similarly be performed once the fibers have been dried, naturally or otherwise.

The drying step of the process of the invention may be performed with a hood, a hairdryer, a straightening iron, a Climazon, etc.

When the drying step is performed with a hood or a hairdryer, the drying temperature is between 30 and 110° C. and preferably between 50 and 90° C.

When the drying step is performed with a straightening iron, the drying temperature is between 110 and 220° C. and preferably between 140 and 200° C.

EXAMPLES

Example 1: Preparation of the Silicone Emulsion 450 g of fluid aminosilicone (copolymer of dimethylsiloxane-aminoethylaminopropylmethylsiloxane comprising trimethylsilyl end groups, having an amine number of 7.2 mg of KOH/g and a viscosity of 5600 mPa·s at 25° C.) are transferred into a 1st vessel; 1800 g of dimethylsiloxane comprising trimethylsilyl end groups, having a viscosity of 61 500 mPa·s at 25° C., are added, with stirring, and the stirring is maintained for 2 hours at ambient temperature.

In a separate vessel, 49 g of steareth-6 and 62 g of PEG100 stearate are mixed, and the mixture is heated to 60° C. The mixture is maintained at this temperature until a liquid mixture is obtained, then 31 g of trideceth-3 and 350 g of trideceth-10 (80% of active material) are added. The surfactant mixture has an HLB=11.25. 80 g of water and 6.2 g of glacial acetic acid are added and the stirring is continued until a creamy paste is obtained.

The content of this 2nd vessel (creamy paste) is then transferred into the 1st vessel (containing the silicones), then the mixture obtained is mixed for 30 minutes at ambient temperature (20-25° C.). The mixing steps are carried out in order to obtain a homogeneous mixture; they are carried out at ambient temperature.

79.6 g of demineralized water are added and mixing is carried out for 60 minutes.
72.7 g of demineralized water are added and mixing is carried out for 50 minutes.
197.4 g of demineralized water are added and mixing is carried out for 5 minutes.
294.3 g of demineralized water are added and mixing is carried out for 5 minutes.
180 g of demineralized water are added and mixing is carried out for 5 minutes.
180 g of demineralized water are added and mixing is carried out for 5 minutes.
197.4 g of demineralized water are added and mixing is carried out for 5 minutes.
197.4 g of demineralized water are added and mixing is carried out for 3 minutes.
228.5 g of demineralized water are added and mixing is carried out for 3 minutes.

Finally, 40.5 g of 2-phenoxyethanol (preservative) are added and mixing is carried out for 3 minutes.

An oil-in-water emulsion having a particle size $D_{50}$ of 170 nm is obtained.

Example 2

Compositions (g AM/100 g)

| Composition | A |
|---|---|
| VA/crotonates/vinyl neodecanoate copolymer | 2 |
| Carbomer | 0.75 |
| Silicone emulsion as prepared in example 1 | 2 |
| Synthetic mica and titanium dioxide and Red 7 calcium lake on barium sulfate substrate | 7 |
| Neutralizers | qs |
| Preservative, fragrance | qs |
| Ethanol | 7.5 |
| PEG-40 hydrogenated castor oil | 1 |
| Water | qs 100 |

Protocol

Composition A is applied to locks of yak hair at a rate of 1 g of composition per gram of lock. The locks are then combed, dried with a hairdryer and then combed again.

Results: "Cosmetic Feel" Performance

The performance levels in terms of cosmetic feel were evaluated on dried locks by five experts, in a blind test.

In 100% of the cases, the experts judged that composition A according to the invention afforded smooth locks with clearly individualized hair strands, having a pleasant cosmetic feel, especially good softness, good suppleness and absence of tackiness.

Example 3

Compositions (g AM/100 g)

| | A1 Invention | B1 comparative | C1 comparative |
|---|---|---|---|
| Phenoxyethanol | 0.7 | 0.7 | 0.7 |
| Silicone emulsion as prepared in example 1 | 2 | 2 | 2 |
| CI 77891 (and) synthetic fluorophlogopite (and) CI 15850 | 10 | 10 | 10 |
| VA/crotonates/vinyl neodecanoate copolymer | 3 | — | — |
| Carbomer | 0.75 | 0.75 | 0.75 |
| Polyvinylcaprolactam | — | 3 | — |
| VP/dimethylaminoethyl methacrylate copolymer | — | — | 3 |
| Ethanol | 7.5 | 7.5 | 7.5 |
| water | qs 100 | qs 100 | qs 100 |
| PEG-40 Hydrogenated castor oil | 1 | 1 | 1 |

Protocol

Composition A1, B1 or C1 is applied to locks of yak hair at a rate of 1 g of composition per gram of lock.

The locks are dried with a hairdryer and then combed.

The locks are then rubbed on a white cloth.

Results: "Transfer-resistance" Performance

The performance levels in terms of transfer resistance were evaluated by five experts, in a blind test, who visually evaluated the amount of pigment present on the white cloth after rubbing.

In 100% of the cases, the experts judged that composition A1 according to the invention, compared with compositions B1 and C1, led to a very markedly smaller amount of pigment present on the cloth than the amount deposited by compositions B1 and C1. Composition A1 according to the invention thus has better transfer-resistance properties than the comparative compositions B1 and C1.

Example 4

Compositions (g AM/100 g)

| | H Invention | I Comparative |
|---|---|---|
| VA/crotonates/vinyl neodecanoate copolymer | 2 | 2 |
| Carbomer | 0.75 | 0.75 |
| Silicone emulsion as prepared in example 1 | 2 | — |
| Synthetic mica and titanium dioxide and Red 7 calcium lake on barium sulfate substrate | 7 | 7 |
| Neutralizers | qs | qs |
| Preservative, fragrance | qs | qs |
| Ethanol | 7.5 | 7.5 |
| PEG-40 hydrogenated castor oil | 1 | 1 |
| Water | qs 100 | qs 100 |

Protocol

Compositions H and I are applied to locks of yak hair at a rate of 1 g of composition per gram of lock.

The locks are then combed, dried with a hairdryer and then combed again.

Results No. 1: Coloring Performance Levels

The performance levels in terms of uniformity of color intensity were evaluated on dried locks by 5 experts, in a blind test.

100% of the experts found that the lock treated with composition H according to the invention has a more intense and more uniform color result than comparative composition I.

Results No. 2: Natural Feel, Suppleness and Individualization

The performance levels in terms of natural feel were evaluated on dried locks by 5 experts, in a blind test.

Action

The expert seizes the lock between the thumb and index finger and slides the fingers along the lock from the upper part to the ends. At the same time, the expert performs a slight oscillating movement with the thumb so as to get a good feeling of the possible presence of deposit or of roughness (unnatural feel).

The expert also evaluates whether the hairs separate from one another, whether they are in packets (non-individualized hair strands).

In 100% of the cases, the experts judged that composition H according to the invention afforded locks that are more individualized and have a more natural feel with, especially, good suppleness, compared with formula I according to the prior art.

The invention claimed is:

1. A composition for dyeing hairs comprising:
a) from 1% to 3% by weight, relative to the total weight of the composition, of vinyl acetate/crotonates/vinyl neodecanoate copolymer,
b) from 1% to 8% by weight, relative to the total weight of the composition, of at least one oil-in-water emulsion having a particle size D50 of less than 350 nm and which comprises:
   a silicone mixture comprising:
      (i) at least one polydialkylsiloxane comprising trialkylsilyl end groups of formula (I):

$$R'_3SiO(R'_2SiO)_p SiR'_3, \quad (I)$$

wherein:
   R', which may be identical or different, is a monovalent hydrocarbon-based radical having from 1 to 18 carbon atoms, and
   p is an integer ranging from 500 to 2 000,
and having a viscosity at 25° C. ranging from 40,000 to 100,000 mPa·s, and
      (ii) at least one aminosilicone of formula (II):

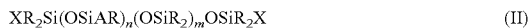

$$XR_2Si(OSiAR)_n(OSiR_2)_m OSiR_2X \quad (II)$$

wherein:
   R, which may be identical or different, is a monovalent hydrocarbon-based radical having from 1 to 18 carbon atoms,
   X, which may be identical or different, represents R or a hydroxyl (OH) or a $C_1$-$C_6$ alkoxy group;
   A is an amino radical of formula $-R_1-[NR^2-R^3-]_xNR^2_2$, or the protonated form of this amino radical, with
      $R^1$ representing a $C_1$-$C_6$ alkylene radical,
      $R^2$, which may be identical or different, being a hydrogen atom or a $C_1$-$C_4$ alkyl radical,
      $R^3$ being a $C_1$-$C_6$ alkylene radical, and
      x being 0 or 1;
   m and n are integers such that m+n ranges from 50 to 1000;
   and having a viscosity at 25° C. ranging from 1000 to 15000 mPa·s and an amine number ranging from 2 to 10 mg of KOH per gram of aminosilicone;
   a surfactant mixture comprising one or more nonionic surfactants, said mixture having an HLB ranging from 10 to 16, and
   water, and
c) at least one pigment.

2. The composition according to claim 1, comprising (i) at least one polydialkylsiloxane comprising trialkylsilyl end groups, having a viscosity, at 25° C., ranging from 40000 to 100000 mPa·s, in an amount of from 70% to 90% by weight, and (ii) one or more aminosilicones having a viscosity, at 25° C., ranging from 1000 to 15000 mPa·s and an amine number ranging from 2 to 10 mg of KOH per gram of aminosilicone, in an amount of from 10% to 30% by weight relative to the total weight of the silicone mixture.

3. The composition according to claim 1, wherein the surfactant mixture comprises one or more nonionic surfactants chosen from:
(i) (poly)oxyalkylenated fatty alcohols of formula: $R_3-(OCH_2CH_2)_c OH$ in which:
   $R_3$ represents a linear or branched alkyl or alkenyl radical comprising from 40 carbon atoms, optionally substituted with at least one hydroxyl group; and
   c is an integer ranging from 1 to 200;
(ii) (poly)oxyalkylenated ($C_8$-$C_{32}$)alkyl phenyl ethers, comprising from 1 to 200 mol of ethylene oxide;
(iii) polyoxyalkylenated esters of $C_8$-$C_{32}$ fatty acids and of sorbitan; or
(iv) polyoxyethylenated esters of $C_8$-$C_{32}$ fatty acids.

4. The composition according to claim 1, wherein the oil-in-water emulsion comprises:
   the surfactant mixture in a total amount ranging from 5% to 15% by weight, relative to the total weight of the emulsion; and/or
   at least one nonionic surfactant in a total amount ranging from 5% to 15% by weight, relative to the total weight of the emulsion; and/or
   the silicone mixture in a total amount ranging from 40% to 60% by weight, relative to the total weight of the emulsion; and/or
   the polydialkylsiloxane(s) comprising trialkylsilyl end groups, in a total amount ranging from 35% to 45% by weight, relative to the total weight of the emulsion; and/or
   the aminosilicone(s) in a total amount ranging from 5% to 15% by weight, relative to the total weight of the emulsion; and/or
   water in a total amount ranging from 25% to 50% by weight, relative to the total weight of the emulsion.

5. The composition according to claim 1, wherein the oil-in-water emulsion has a particle size D50 ranging from 100 to 300 nm.

6. The composition according to claim 1, wherein the composition comprises the oil-in-water emulsion in an amount ranging from 1.5% to 5% by weight, relative to the total weight of the composition.

7. The composition according to claim 1, wherein the weight ratio of the total amount of at least one vinyl acetate/crotonates/vinyl neodecanoate copolymer to the total amount of oil-in-water emulsion ranges from 0.1 to 10.

8. The composition according to claim 1, wherein the composition further comprises a thickener chosen from crosslinked copolymers of acrylic and/or methacrylic acid.

9. A method for dyeing keratin fibers comprising applying to the keratin fibers a composition comprising:
a) from 1% to 3% by weight, relative to the total weight of the composition, of vinyl acetate/crotonates/vinyl neodecanoate copolymer,
b) from 1% to 8% by weight, relative to the total weight of the composition, of at least one oil-in-water emulsion having a particle size D50 of less than 350 nm and which comprises:
   a silicone mixture comprising:
      (i) at least one polydialkylsiloxane comprising trialkylsilyl end groups of formula (I):

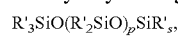

$$R'_3SiO(R'_2SiO)_p SiR'_3, \quad (I)$$

wherein:
R', which may be identical or different, is a monovalent hydrocarbon-based radical having from 1 to 18 carbon atoms, and
p is an integer ranging from 500 to 2 000, and having a viscosity at 25° C. ranging from 40,000 to 100,000 mPa·s and
(ii) at least one aminosilicone of formula (II):

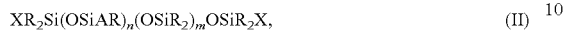

wherein:
R, which may be identical or different, is a monovalent hydrocarbon-based radical having from 1 to 18 carbon atoms,
X, which may be identical or different, represents R or a hydroxyl (OH) or a $C_1$-$C_6$ alkoxy group;
A is an amino radical of formula —$R^1$—[$NR^2$—$R^3$—]$xNR^2_2$, or the protonated form of this amino radical, with
$R^1$ representing a $C_1$-$C_6$ alkylene radical,
$R^2$, which may be identical or different, being a hydrogen atom or a $C_1$-$C_4$ alkyl radical,
$R^3$ being a $C_1$-$C_6$ alkylene radical,
x being 0 or 1;
m and n are integers such that m+n ranges from 50 to 1000;
and having a viscosity at 25° C. ranging from 1000 to 15000 mPa·s and an amine number ranging from 2 to 10 mg of KOH per gram of aminosilicone;
a surfactant mixture comprising one or more nonionic surfactants, said mixture having an HLB ranging from 10 to 16, and
water, and
c) at least one pigment.

10. The composition according to claim 1, wherein the composition comprises said vinyl acetate/crotonates/vinyl neodecanoate copolymer in an amount ranging from 1% to 2% by weight, relative to the total weight of the composition.

* * * * *